United States Patent
Kreissig et al.

(10) Patent No.: US 11,109,923 B2
(45) Date of Patent: Sep. 7, 2021

(54) TROCAR HOLDER

(71) Applicant: avateramedical GmbH, Jena (DE)

(72) Inventors: Albrecht Kreissig, Stuttgart (DE); Leif Pudewills, Esslingen (DE); Tobias Waibel, Ostfildern (DE); Tobias Keim, Wurzbach (DE)

(73) Assignee: avateramedical GmbH, Jena (DE)

( * ) Notice: Subject to any disclaimer, the term of this patent is extended or adjusted under 35 U.S.C. 154(b) by 195 days.

(21) Appl. No.: 16/446,452

(22) Filed: Jun. 19, 2019

(65) Prior Publication Data
US 2020/0000532 A1    Jan. 2, 2020

(30) Foreign Application Priority Data

Jun. 27, 2018  (DE) .................. 102018115435.6

(51) Int. Cl.
| | | |
|---|---|---|
| A61B 34/30 | (2016.01) | |
| A61B 90/57 | (2016.01) | |
| A61B 17/34 | (2006.01) | |
| A61B 17/00 | (2006.01) | |

(52) U.S. Cl.
CPC .......... *A61B 34/30* (2016.02); *A61B 17/3423* (2013.01); *A61B 90/57* (2016.02); *A61B 2017/00367* (2013.01); *A61B 2017/00477* (2013.01); *A61B 2034/302* (2016.02)

(58) Field of Classification Search
CPC ....... A61B 19/201; A61B 19/20; A61B 19/22; A61B 19/203; A61B 19/5244; A61B 17/34; A61B 17/3421; A61B 17/3403; A61B 17/3423; A61B 17/3462; A61B 34/30
See application file for complete search history.

(56) References Cited

U.S. PATENT DOCUMENTS

| | | | | |
|---|---|---|---|---|
| 5,792,135 | A | * | 8/1998 | Madhani .......... A61B 17/00234 606/1 |
| 5,817,084 | A | * | 10/1998 | Jensen .................. A61B 34/71 606/1 |
| 2006/0225529 | A1 | | 10/2006 | Fischer et al. |
| 2008/0122148 | A1 | | 5/2008 | Frey et al. |
| 2010/0292724 | A1 | | 11/2010 | Ravikumar et al. |
| 2015/0374445 | A1 | | 12/2015 | Gombert et al. |
| 2016/0361122 | A1 | | 12/2016 | Seeber |
| 2018/0168746 | A1 | | 6/2018 | Swayze et al. |

(Continued)

FOREIGN PATENT DOCUMENTS

| | | |
|---|---|---|
| DE | 103 40 151 A1 | 4/2005 |
| DE | 10 2013 002 813 A1 | 8/2014 |
| DE | 10 2016 111 737 A1 | 12/2017 |

(Continued)

*Primary Examiner* — Vi X Nguyen
(74) *Attorney, Agent, or Firm* — Christensen, Fonder, Dardi & Herbert PLLC (57) ABSTRACT

A trocar holder for a manipulator of a robotic surgical system. The trocar holder includes a base element for securing the trocar holder to the manipulator and a clamp element which is replaceably connected to the base element via a coupling mechanism. Two limbs movable relative to each other in a clamp plane are formed on the clamp element. The limbs are connected via a spine and have free tips. The trocar holder also has a clamp mechanism for opening and closing the limbs and a receiving element for a trocar.

19 Claims, 8 Drawing Sheets

(56) References Cited

U.S. PATENT DOCUMENTS

2019/0159851 A1   5/2019   Karguth et al.

FOREIGN PATENT DOCUMENTS

| EP | 1 925 260 A2 | 5/2008 |
| EP | 3 103 410 A1 | 12/2016 |
| EP | 3 111 876 A2 | 1/2017 |
| WO | WO 00/18306 A1 | 4/2000 |
| WO | WO 03/092518 A1 | 11/2003 |
| WO | WO 2013/075205 A1 | 5/2013 |
| WO | WO 2018/001742 A1 | 1/2018 |

* cited by examiner

TROCAR HOLDER

PRIORITY CLAIM

The present application claims priority to German Patent Application No. 10 2018 115 435.6, filed on Jun. 27, 2018, which said application is incorporated by reference in its entirety herein.

FIELD OF THE INVENTION

The invention relates to a trocar holder for a manipulator of a robotic surgical system. Such a trocar holder comprises a base element for securing the trocar holder to the manipulator. It moreover comprises a clamp element with two limbs which are replaceably connected to the base element via a coupling mechanism. The two limbs are movable relative to each other and connected to each other via a spine; they are formed with free tips. Finally, the trocar holder comprises a clamp mechanism for opening and closing the limbs, and thus the clamp.

BACKGROUND OF THE INVENTION

Today, robotic surgical systems are used for an increasing number of minimally invasive operations, in particular in areas which are difficult to access. Such a surgical system as a rule comprises a number of manipulator arms which are coupled to a supporting device at one end and have an instrument support device at the other end. Together they form a manipulator. Control is effected via an operator console, which need not necessarily be located in the immediate vicinity of the manipulators.

Via the operator console the operator, i.e., the surgeon, usually operates several robotically controlled arms, which hold the instruments, in order to carry out individual steps of an operation. The surgeon controls the manipulator arms of the system via the operator console or by corresponding movements via a suitable coupling mechanism which converts movements of the surgeon's hands into movements of the corresponding instrument. The manipulators are multi-element systems in which the individual elements are connected to each other via joints. One group of the elements serves to position the manipulator relative to other manipulators of the same robotic system, with the result that the manipulators do not obstruct each other. This group of the elements is also called the control; the described positioning is effected before the operation and is therefore also called pre-positioning.

Another group of the elements serves to position and guide the tool on the object, thus for example to position a surgical instrument or an endoscope in the area of an opening in the outer tissue of a patient. This group of the elements is also called the instrument support device. The elements of a manipulator are connected to each other in the kinematic sense as an open kinematic chain, as there is no further joint sitting on the last element, just the tool. All the other elements are connected to each other via joints in the manner of a chain.

To carry out minimally invasive procedures, so-called trocars are used; these are medical instruments with which an access into the body is first created, for example into the abdominal cavity. This access is then held open by means of the trocar, which is in the shape of a tube. The tube serves to insert surgical instruments, or also endoscopic cameras, into the body. During the operation the trocar should not alter its position, i.e., should remain stably arranged in a predefined position, unless something else is required.

Trocars are also used in robotic surgical systems and are held in position during the operation. The instrument support devices for this are as a rule equipped with a trocar holder, by which the instrument can then be guided into the body. After a pre-positioning of the trocar holders on the various manipulators of the robotic surgical system, the trocars and then the instruments can be inserted. Care is to be taken here that the stress on the tissue at the points where the trocars are inserted is kept as low as possible. In addition, the area of the trocar holders and of the trocars is to be kept sterile. Trocars can be designed as disposable or reusable components; the same applies to the trocar holders. It is important that the trocar holders can likewise be changed, for example in order to prepare for a new operation or to attach a different trocar.

The clamp element is usually secured to the manipulator via the base element in such a way that a relative movement between the two is ruled out in the assembled or connected state, as an electrical contact with an instrument guide or with the manipulator which allows, for example, an electrical opening and closing of the clamp is optionally also produced via the base element. In this case, to adhere to the imperative of using sterile instruments, a sterilization film safeguarding this condition or a similar means is placed in the clamp, which then holds the trocar. As the trocar holder itself is not sterile and yet is guided in relatively close proximity to the patients, in some cases there is an increased risk of infection here.

In connection with robotic surgical systems, various trocar holders are known in the state of the art, with which the trocar can generally be positioned relative to a patient.

In WO 03/092518 A1, in FIGS. 11.A-D, various clamp devices are shown, with which a trocar can be fixed in a corresponding opening of the closed clamp. The instrument itself can then be moved along the trocar axis, which is called the z-axis. Moreover, in FIG. 11.E of WO 03/092518 A1, a coupling mechanism formed as a quick-release fastener for coupling the clamp element to an axially rotatable shaft is shown. The coupling mechanism comprises a push-in connection between the clamp element and the rotatable shaft, as well as a sliding sleeve with a stop position, which surrounds areas of a shaft of the clamp element as well as the rotatable shaft. The rotatable shaft is connected to a motor by means of a bevel gear and can be rotated axially. However, the trocar holder described in WO 03/092518 A1 is not intended for use in a robotic system, but rather serves only to stably position a trocar in laparoscopic operations.

In EP 3 111 876 A2 a clamp device is described which can be used with a robotic surgical system. In the closed state the clamp device directly holds a trocar or trocar holder; to open and close the clamp it has a lever mechanism, as demonstrated for example in FIGS. 19A and 19B of EP 3 111 876 A2. The inside of the clamp can be lined with a sterile cloth. A secure holding is only possible for a particular trocar diameter or a particular diameter of a trocar holder. The clamp can be connected to a manipulator arm via a base element. In this case the trocar or the trocar holder can be moved only in the axial direction; all other adjustments must be effected with the aid of the manipulator arm itself, to which the base element is permanently secured. An adaptation to different trocar diameters is possible in the sense that in the clamp itself only the head of a trocar holder is fixed, to which a tube is attached, which as a rule has a diameter substantially smaller than the head, with the result that different diameters can be realized.

In EP 3 103 410 A1 FIGS. 11, 12 and 15 show a trocar 800 which is mounted tiltably on a trocar holder 17. A device for simple changing of the trocar or the trocar holder is not provided. However, the tiltability makes a more compact design possible and puts less stress on a patient's tissue.

SUMMARY OF THE INVENTION

The object of the invention is to develop a trocar holder for a robotic surgical system of the type described at the outset to the effect that, for one thing, there is a simple replaceability, adaptation can be made more easily to different diameters of trocars, wherein an equally secure hold is to be guaranteed for all diameters, and moreover the stress on the patient is to be kept as low as possible.

This object is achieved according to the invention with a trocar holder of the type described at the outset in that the trocar holder comprises a receiving element for a trocar.

The limbs are opened and closed with the clamp mechanism; when the limbs are opened the trocar, together with the receiving element, can be removed and replaced, for example. In this way, receiving elements for different trocars can be changed without particular effort, for example a receiving element for a trocar which is to receive a scalpel can be replaced by a thicker one for an endoscope. As the receiving elements can be optimally adapted to the various trocars, there is always the best possible hold. The receiving elements can in particular also be permanently connected to the trocars, by being formed integrally for example, preferably from plastic.

When the limbs are closed the receiving element is preferably held by them rotatably about a first rotational axis lying in the clamp plane. In this way, a degree of freedom is realized for the trocar holder in that it is pivotable about a pivot point on its longitudinal axis, whereby a more compact structure is made possible and a reduction in the stress on the patient's tissue when a trocar is inserted is achieved.

In an embodiment, in the area of the tips of each of the two limbs a so-called radial-axial bearing is formed, i.e., a bearing which prevents a shaft or axle both from moving radially and from moving axially in a direction along the axle, for example with the aid of a stop. Through the use of two radial-axial bearings, the axial movement can be limited in both directions along the axle. The receiving element itself is formed as an axle in this case and is clamped by the two radial-axial bearings, with the result that when the limbs are closed the receiving element is prevented from moving axially by the radial-axial bearings. The receiving element has a continuous opening perpendicular through the axle to feed the trocar through. The opening can be a simple annular opening, the internal diameter of which corresponds approximately to the external diameter of the trocar. Depending on the diameter of the trocar, different receiving elements which have different diameters can be used. In this way there is always an optimum hold of the trocar in the receiving element and thus in the trocar holder, as an adaptation to different diameters can be made exactly and without particular effort by means of different receiving elements. This increases the security in the handling of the surgical system.

Usual trocars for robotic surgical systems have an instrument receiver with a rather large diameter and a feed-through element connected thereto with a smaller diameter than the instrument receiver; as a rule the feed-through element is designed as a cylindrical tube. The instrument is therefore prevented from sliding through at least by the instrument receiver; it is mounted therein and optionally also fixed. If, in connection with the invention, specially adapted trocars are used, the tube of which is not formed cylindrical, but in which the feed-through element is in the shape of a truncated cone which tapers protruding from the instrument receiver—thus away from the instrument receiver, wherein the cone angle is chosen to be extremely narrow, with the result that a difference from the cylindrical shape is barely recognizable with the naked eye, then the penetration depth of the trocar can be controlled and at least limited to a limited extent by means of the diameter of the continuous opening in the receiver element.

The coupling mechanism for the connection between base element and clamp element in an embodiment is designed as a quick-release fastener which is operable by hand without further aids. For example, a snap-fit connection is particularly suitable. The base element is then permanently mounted on the manipulator and fixes the clamp element to the base element by means of the snap-fit connection; a relative movement between base element and clamp element is then ruled out. The clamp element itself is then mechanical, i.e., to be operated by hand. A sterile separation between the clamp element and the base element can be achieved by introducing a sterilization film between the two elements before the production of the connection between them. This can be held clamped, for example, between the two elements or connected detachably or permanently to the clamp element. The sterility area can thereby ultimately be placed further away from the patient compared with the state of the art, which improves the hygienic safety. For this, all the parts on the side of the sterilization film facing the patient must be laid out sterile, including at least the receiving element, the clamp element and the clamp mechanism; and the trocar of course.

In an embodiment, at least the receiving element, the clamp element and the base element are manufactured from plastic. Forming them from plastic makes it possible to reduce the costs of production and to provide at least the clamp element and the receiving element also as disposable parts, i.e., for single use, which further improves the hygiene conditions.

The two limbs and the spine of the clamp element are particularly preferably formed in one piece. In particular when the limbs and spine are formed integrally, but also in the case of other types of connection, for example a screw or adhesive connection, the clamp formed of limbs and spine advantageously has a spring effect, which has the result that in the case of elastic deflection out of a rest position, a zero position in which no restoring force is acting, the limbs elastically spring back into it, if the force effect necessary for the deflection ceases or if they are no longer held in their deflected position. At least one of the limbs is therefore advantageously connected to the spine in a spring-loaded manner. The elastic deflection out of the zero position is effected by means of a force effect, which can be exerted for example by the clamp mechanism.

The clamp mechanism can be realized in a different way, wherein care must be taken that the receiving element with the trocar is held securely and is protected from inadvertent release. In an expedient embodiment, the clamp mechanism comprises at least one pin, which is fixed at an angle different from zero relative to the clamp plane in the limb in question. Moreover, the clamp mechanism then comprises a guide element, movable along or about a movement axis relative to the clamp element, in which at least one elongated hole with narrow sides and long sides is made. The number of elongated holes corresponds to the number of pins, wherein one pin can be provided in each of the limbs. The at least one pin, which is preferably manufactured from metal, in particular stainless steel, is guided in the at least one elongated hole, wherein the two narrow sides of the at least one elongated hole lie at different distances from the movement axis, with the result that the at least one limb—corresponding to the number of pins—opens or closes during movement of the guide element along or about the movement axis. Preferably two pins are used, i.e., one pin is fixed in each of the two limbs, preferably perpendicular to the clamp plane. This increases the stability and improves handling.

Through the movement of the guide element, a relative movement between pin and elongated hole is effected, which is limited by the narrow sides of the elongated hole. If the pin is located on the narrow side lying closer to the movement axis, the clamp or the limb in question is closed. If the pin is located on the other narrow side of the elongated hole, the clamp or the limb is opened.

The clamp mechanism can then be realized in different manners. In a possible design, the movement axis lies in the clamp plane and is spaced apart equally from both—as a rule symmetrical—limbs, thus lies precisely in the centre between the two. In this case the guide element is formed as a guide carriage which is displaceable along the movement axis. The at least one elongated hole can be designed straight in order to achieve a linear opening or closing of the clamp in relation to the displacement, i.e., the distance covered. Other, curved elongated holes are possible in order for example to reduce the effort during increasing opening, which means that during increasing opening the displacement distance of the carriage becomes greater for a predefined angle, as the curvature is reduced.

The clamp mechanism can be designed even more compact if the movement axis is formed as a second rotational axis, which forms an angle different from zero, preferably a right angle, with the clamp plane. In this case the guide element is rotatable about the second rotational axis, wherein the at least one elongated hole—which is also called a slotted link—is at least partially curved. The second rotational axis preferably runs through the guide element.

By rotating the guide element about the second rotational axle—in the case of the exemplary but non-limiting use of two pins—the pins are moved back and forth in the two elongated holes between the end positions, i.e., the narrow sides of the elongated holes, depending on the direction of rotation. The narrow sides of the elongated holes that have the shortest radial distance from the second rotational axle then define the state of a closed clamp or closed limbs; here the pins are closest to the second rotational axis of the guide element. The other narrow sides, which lie furthest removed from the second rotational axis, then define the position of the opened clamp or opened limbs. It is not strictly necessary that both pins in each case also actually reach the end positions, i.e., the narrow sides; what is important is that the movement of the guide element results in a relative movement of the two limbs towards each other or away from each other, if the direction of movement is reversed.

In principle, it is sufficient if only one limb is provided with a pin and the guide element has a single elongated hole, in which the pin is guided. Already in this way the clamp can be opened and closed by moving one limb away from the other or towards it in the clamp plane.

However, it is advantageous to provide two elongated holes with two pins; on the one hand this makes it possible to open the clamp wider if the distances between the narrow sides of the elongated holes in relation to the movement axis remain the same, in comparison with the use of only one elongated hole. On the other hand, this increases the stability of the system and makes handling easier, as the deflection of the two limbs to achieve the same distance between the tips of the limbs turns out to be less compared with the movement of only one limb, with the result that the effort can be reduced and the material fatigue due to the elastic deformation during bending is reduced.

Here a clamp mechanism in which the pins—and, where the movement axis is also formed as a rotational axis, also the rotational axis—are arranged perpendicular to the clamp plane is expedient and particularly simple to operate.

In order to prevent the clamp mechanism from opening or closing involuntarily when, for example, the trocar is moved, the at least one pin can have an interference fit in relation to the at least one elongated hole, which is dimensioned such that a mechanical displacement with minimum input of force is still possible without exertion by a user.

In the event that the movement axis is a second rotational axis, about which the guide element is rotatable, the latter can particularly advantageously be rotatably secured on a tongue connected to the clamp element, which is particularly expediently secured to the spine of the clamp element. The tongue can be formed integrally with the spine. The rotatable guide element has the advantage over the displaceable one that it is always arranged in the same area of the clamp element, whereby a compact arrangement and likewise the securing to the clamp element itself is possible in a simple, compact manner; this securing additionally fixes the second rotational axis and further stabilizes the device.

In another embodiment, on the longitudinal side that faces the movement axis the at least one elongated hole in the guide element has an indentation in the direction of the movement axis, in which the at least one pin engages when the limbs are opened, in the area of the narrow side lying further removed from the movement axis. This is particularly useful when spine and limbs are formed integrally and, because of the elastic bending during opening of the limbs, the pins are pressed into the indentations because of the restoring force. The opened position is thus better fixed and handling when receiving elements are changed becomes more secure.

The guide element expediently has a lever for actuating the clamp mechanism, in particular when the movement axis is formed as a second rotational axis. The lever then grips the rotational axis on one side and extends away from it in a substantially radial direction. When the lever is actuated the guide element is thus rotated about the rotational axis.

On the lever and on the clamp element, fixing means corresponding to each other are preferably formed, for example as a snap-on connection, by means of which the lever is secured in its position at least when the limbs are closed. This additionally hinders the possibility of involuntary opening, but also secures the trocar holder against unintentional opening when touched by accident.

In a top view projected onto the clamp plane the lever is then preferably located inside the contour of the clamp element or terminates flush with it, which likewise represents an additional securing against unintentional opening.

In a further embodiment, the receiving element is permanently connected to a trocar (18) and preferably formed integrally with it. The trocar can thus be prevented from accidentally slipping out of the receiving element.

A modification of the clamp mechanism with a guide element rotatable about the second rotational axis forming an angle different from zero with the clamp plane results when, instead of pins, at least one eccentric element arranged eccentrically relative to the second rotational axis is attached to the guide element, with the result that at least one of the limbs opens or closes due to the action of the eccentric element when the guide element is rotated about the second rotational axis. The eccentric element can be arranged or formed separately on the guide element—preferably formed like a disc—but it can also be part of the level handle, in that it has a correspondingly varying curvature in the area in which it is connected to the guide element. In the closed state the at least one eccentric element is then not in contact with the corresponding limb or only lies against it, with the result that the limb is not under pretension. By rotation of the guide element the eccentric element is then guided into the area of the limb and presses it away from the second rotational axis in the clamp plane. Here also, two eccentric elements are preferably used which can, however, be formed integrally with the lever.

It is understood that the features mentioned above and those yet to be explained below can be used not only in the stated combinations but also in other combinations or alone, without departing from the framework of the present invention.

BRIEF DESCRIPTION OF THE DRAWINGS

The invention is explained in even more detail below by way of example with reference to the attached drawings, which also disclose features essential to the invention. There are shown in:

FIGS. 1A), B) the overall view of a robotic surgical system,

DETAILED DESCRIPTION

Figure 1:
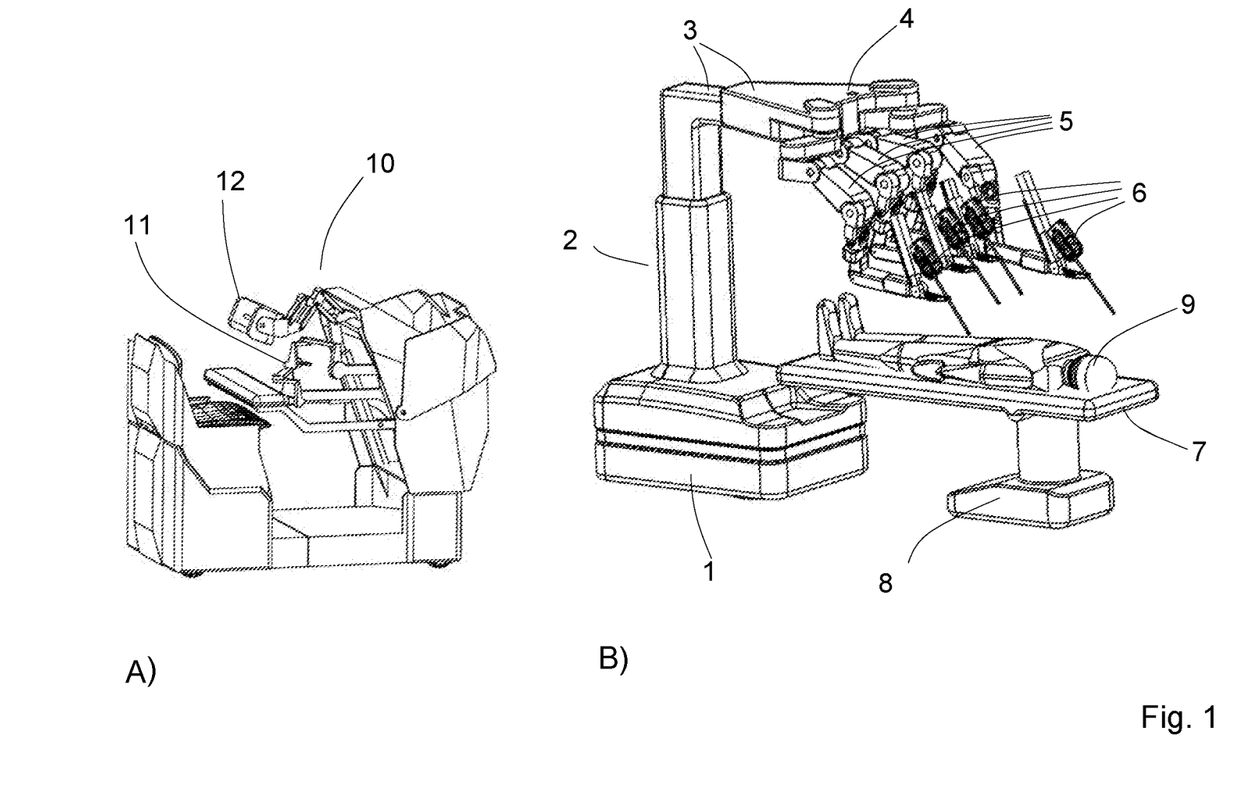

FIG. 1 first shows a robotic surgical system in an overall representation. FIG. 1B) shows the support structure of the robotic surgical system, which rests on a pedestal 1, on which a height-adjustable supporting column 2 is arranged, with a boom 3 protruding therefrom and a fork structure 4 on the free end of the boom 3. By way of example, a total of four manipulators 5 with instrument holders 6 are arranged on the boom 3 with the fork structure 4. Underneath the manipulators 5 with instrument holders 6, an operating table 7 is arranged on a table pedestal 8, on which a patient 9 to be operated on is located. The operating table 7 can be mounted rotatably on the table pedestal 8. The support structure of the robotic surgical system and the operating table 7 can advantageously also be moved translationally relative to each other.

The robotic surgical system also has a control device 10, which is shown in FIG. 1A) and is likewise mobile, here movable relative to the support structure. It is operated by a specially trained surgeon, and the movements of the surgeon on the handles 11 of the control device 10 are transferred to the manipulators 5 or to instruments held in the instrument holders 6. The surgeon can monitor the operating area with the aid of a viewing device 12.

The manipulator 5 is a multi-element system which corresponds to a loose kinematic chain. One group of the elements form a positioning device—also called the manipulator arm—and the remaining group of the elements form an instrument support device; the instrument holder 6 is mounted on the latter.

Figure 2:
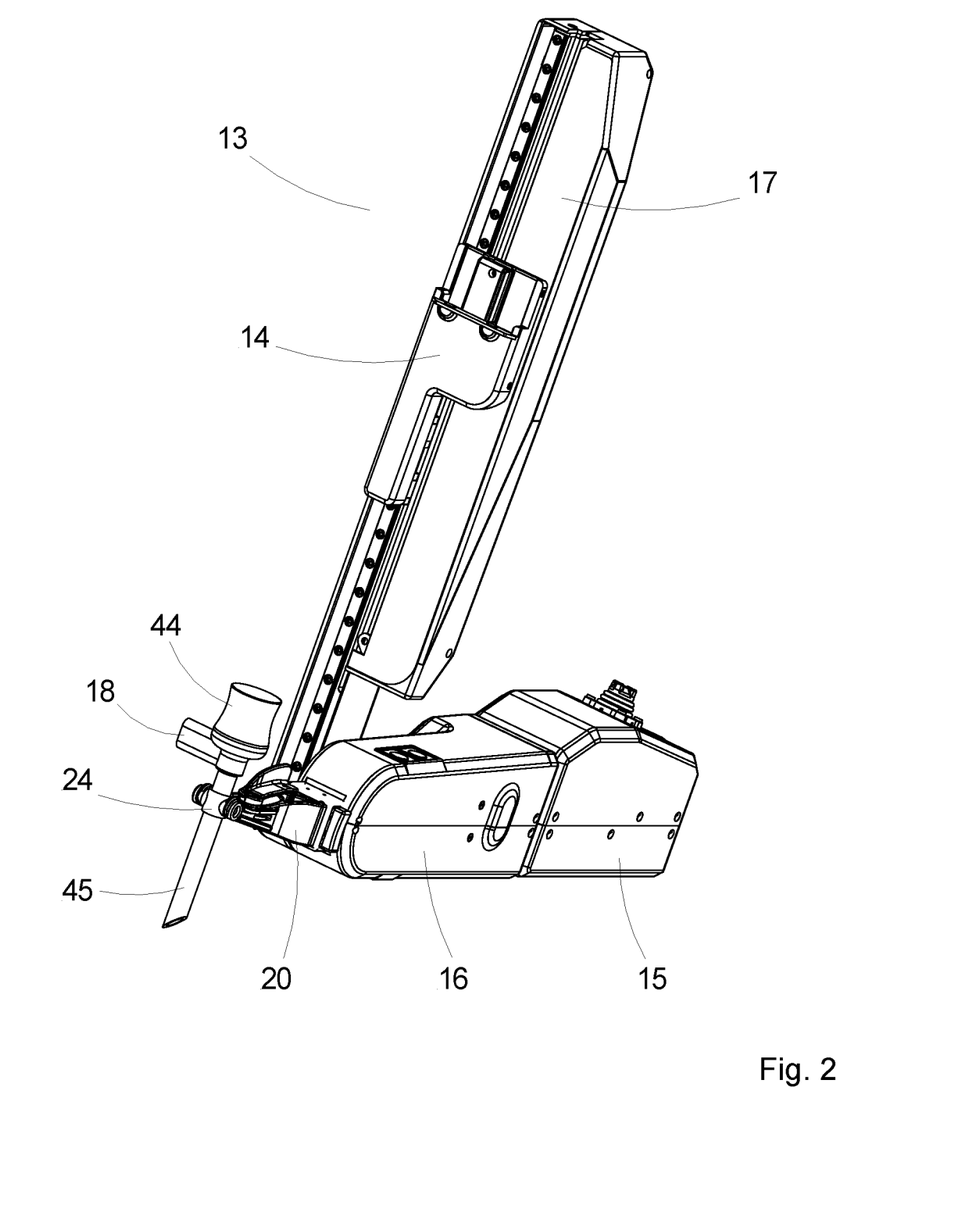
FIG. 2 an instrument support device with a trocar holder and trocar in perspective view, FIG. 3 a trocar holder with trocar in perspective view, FIG. 4 an exploded drawing of the trocar holder with trocar, FIG. 5A) a clamp element of the trocar holder from below, FIG. 5B) a receiving element of the trocar holder from below, FIG. 5C) a guide element of the trocar holder from below, FIGS. 6A), B) the trocar holder in the closed state from above and below, FIG. 7 the clamp element with an inserted receiving element in the closed state, FIG. 8 the clamp element with receiving element removed therefrom in the opened state, and FIG. 9 a trocar holder with trocar and sterilization film.

FIG. 2 shows such an instrument support device 13, but without instrument holder 6. The instrument holder 6 is coupled to the instrument support device 13 via a translationally movable carriage 14. The instrument support device 13 comprises a first arm element 15, with which the instrument support device 13 is coupled to the positioning device of the manipulator 5. It furthermore comprises a second arm element 16, which is rotatable relative to the first arm element 15 about a common longitudinal axis. The second arm element 16 connects the first arm element 15 to a third arm element 17, which is rotatable about an axis oriented perpendicular to the common longitudinal axis of the first and second arm elements. In the extension from the first arm element 15 and the second arm element 16, a trocar holder with a trocar 18 is attached to the tip of the second arm element 16; the trocar holder is explained in more detail below substantially with reference to the perspective views of FIGS. 3 and 4. FIGS. 5A)-C) show individual parts of the trocar holder in detail, FIGS. 6A)-B) show the closed trocar holder in two views, while FIG. 7 and FIG. 8 demonstrate the opening and closing of the trocar holder.

Figure 3:
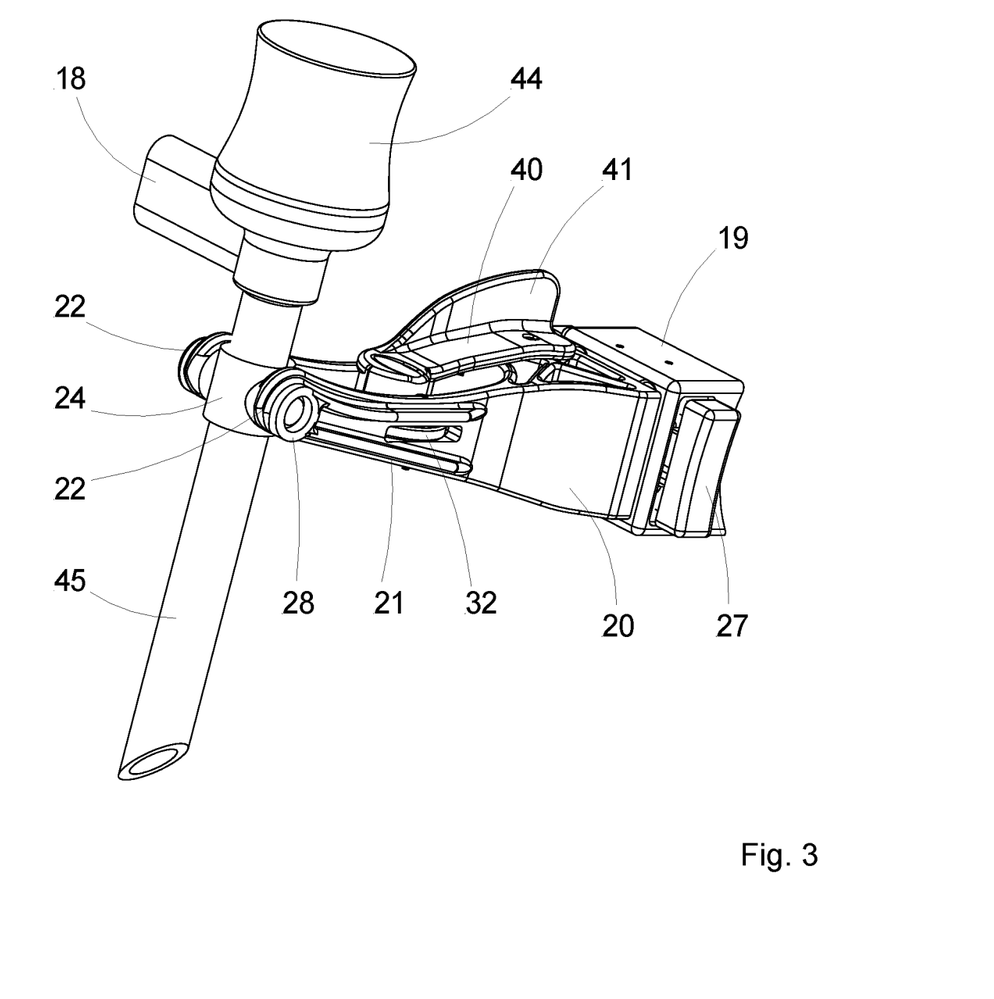

FIG. 3 shows the trocar holder from FIG. 2 with a trocar 18, but without instrument support device 13. The trocar holder comprises a base element 19 for securing the trocar holder to the manipulator 5 or the instrument support device 13 of the manipulator 5. The trocar holder moreover comprises a clamp element 20, which is replaceably connected to the base element 19 via a coupling mechanism. Two limbs 21 movable relative to each other in a clamp plane with free tips 22 are formed on the clamp element 20. Moreover, the clamp element 20 has a clamp mechanism for opening and closing the limbs 21. The limbs 21 are connected at their ends lying opposite the tips 22 by means of a spine 23. Finally, the trocar holder comprises a receiving element 24 for the trocar 18; when the limbs 21 are closed, the receiving element 24 is held by them rotatably about a first rotational axle lying in the clamp plane.

The coupling mechanism for connecting the base element 19 to the clamp element 20 is operable by hand without further aids and is formed as a quick-release fastener, here as a snap-fit connection. For this, there is a snap-fit element 25, on which one or more snap-fit catches 26 are formed, on the clamp element 20. On the base element 19 there is an opening—not represented here—into which the snap-fit element 25 is inserted and correspondingly engages. To quickly release the snap-on connection there are, on the base element 19, two mechanical push buttons 27, which are pressed together to release the snap-fit connection. This can be done with one hand; the other hand can hold the clamp element 20. Before operation, before clamp element 20 and base element 19 are put together, a sterilization film is placed between them, which is fixed in the assembled state by the snap-fit connection.

The two limbs 21 are movable relative to each other in a clamp plane. The clamp plane is the plane in which the two limbs lie and in which the relative movement of the limbs is also generated by means of the clamp mechanism. At least one of the two limbs is thus moved when the clamp mechanism is actuated.

The first rotational axis, about which the trocar 18 can rotate, also lies in the clamp plane. In order to make rotation possible, a radial-axial bearing 28 is formed in the area of the tips 22 of each of the two limbs 21. The receiving element 24 is formed as an axle and is prevented from moving axially by the radial-axial bearings 28 when the limbs are closed. For this, it lies with the axle's end areas 29 in the radial-axial bearings 28. Moreover, the receiving element 24 has a continuous opening 30 perpendicular through the axle to feed the trocar 18 through. The trocar 18 is inserted in this. The receiving element 24 is replaceable and can be provided in different sizes, i.e., with openings of different diameter. In this way, an optimum adaptation to the respective trocar 18 is always possible, as different trocars can be used for different instruments. Trocars for endoscopes are, for example, somewhat thicker than trocars for scissors or scalpels.

The trocar 18 has an instrument receiver 44, to which a feed-through element 45 is connected protruding therefrom. The feed-through element 45 has a tapering truncated cone shape protruding from the instrument receiver 44. The cone angle is extremely acute, preferably less than 1°, particularly preferably less than 0.1°; in this way a corresponding penetration depth can be predefined: the more acute the cone angle, the greater the penetration depth, if the same receiving element 24 is used. As the cone shape is very pointed, a secure seat of the trocar 18 in the receiving element 24 is still made possible.

The limbs and the spine of the clamp element are preferably formed in one piece and are preferably manufactured from plastic. This makes it possible on the one hand to have low production costs and on the other hand to design the clamp element as a disposable article, which is disposed of after each operation, which is advantageous in terms of hygiene.

In particular when the limbs 21 and the spine 23 are formed integrally, but also in the case of other types of connection, for example a screw or adhesive connection, the clamp formed of the limbs and the spine preferably has a spring effect, which has the result that when elastically deflected out of a rest position, which here can be that represented in FIG. 5A) for example, the limbs 21 elastically spring back into it, if the force effect necessary for the deflection ceases or if they are no longer held in their deflected position. At least one of the limbs 21 is therefore advantageously connected to the spine 23 in a spring-loaded manner in order to generate this spring effect. The rest position can in principle be chosen freely and is not subjected to restrictions, for example in the case of injection moulding, i.e., the limbs need not necessarily lie parallel in the rest position, as shown in FIG. 5A), but can also converge or diverge slightly towards their tips 22.

In the case of a spring effect of the clamps the receiving element 24 can in principle also be inserted by hand into the radial-axial bearing 28 at the tips 22 of the limbs 21, but this is time-consuming and inconvenient, and the clamp element 21 can also be destroyed if handled incorrectly.

Figure 4:
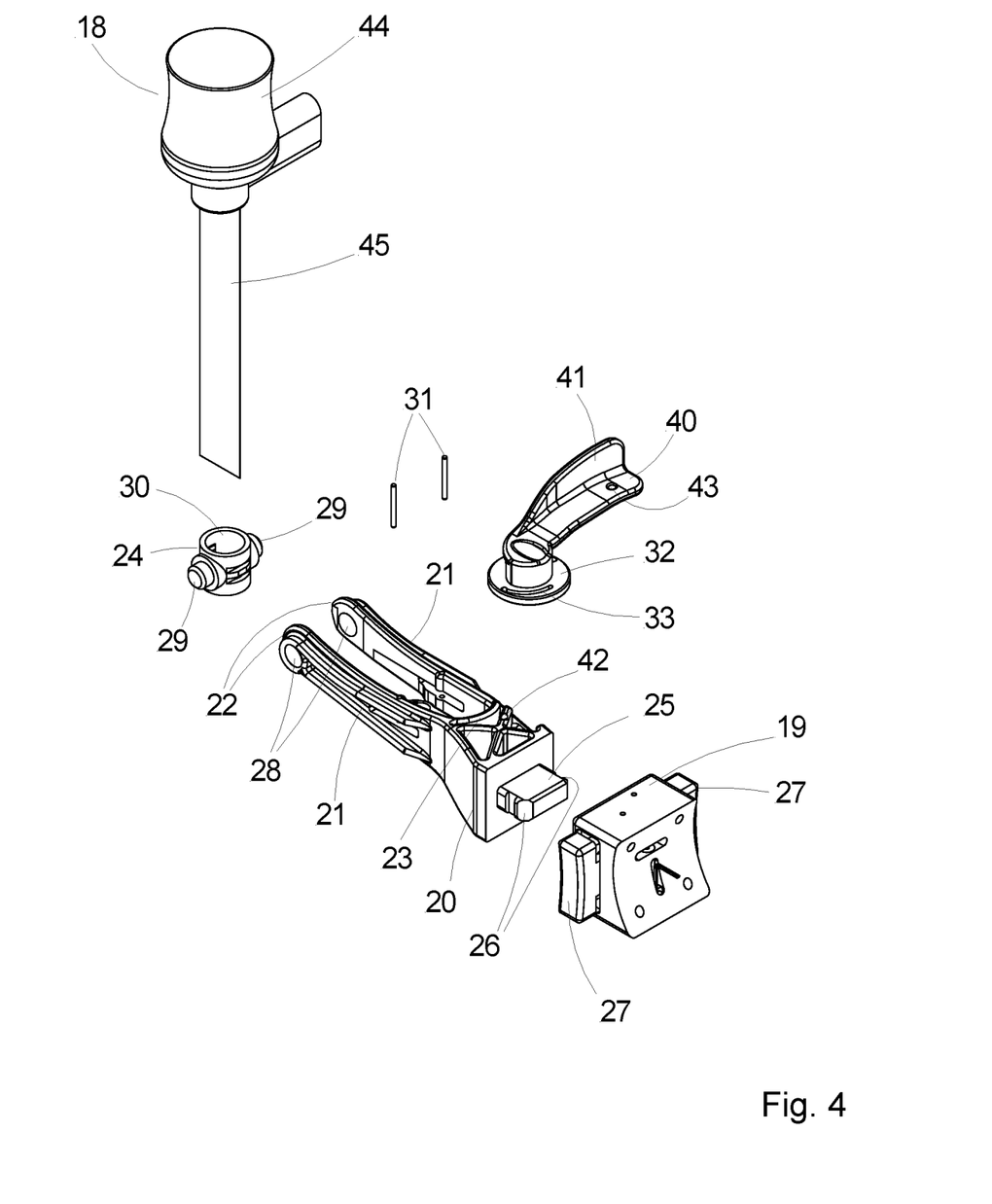
Figure 5:
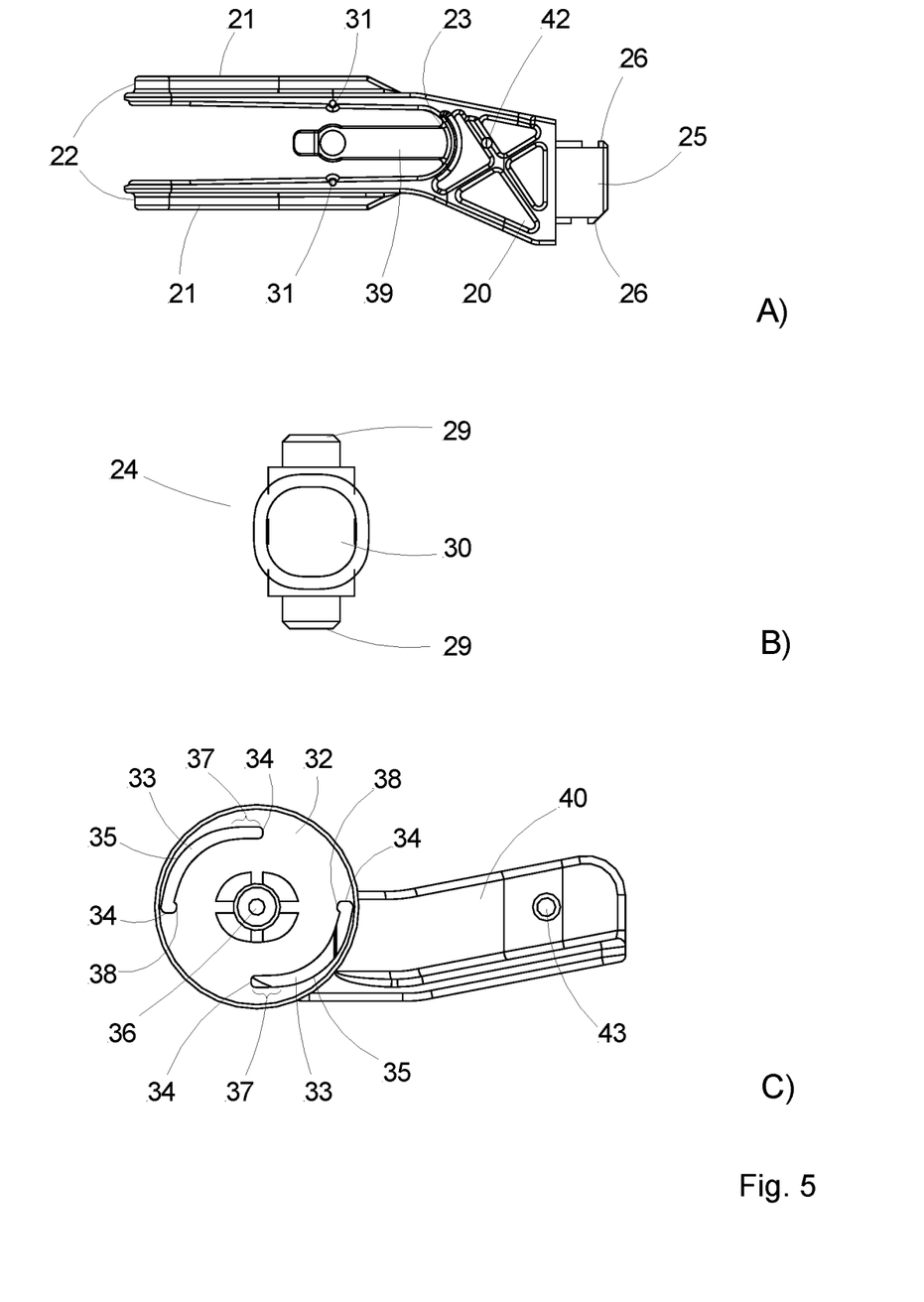
Figure 6:
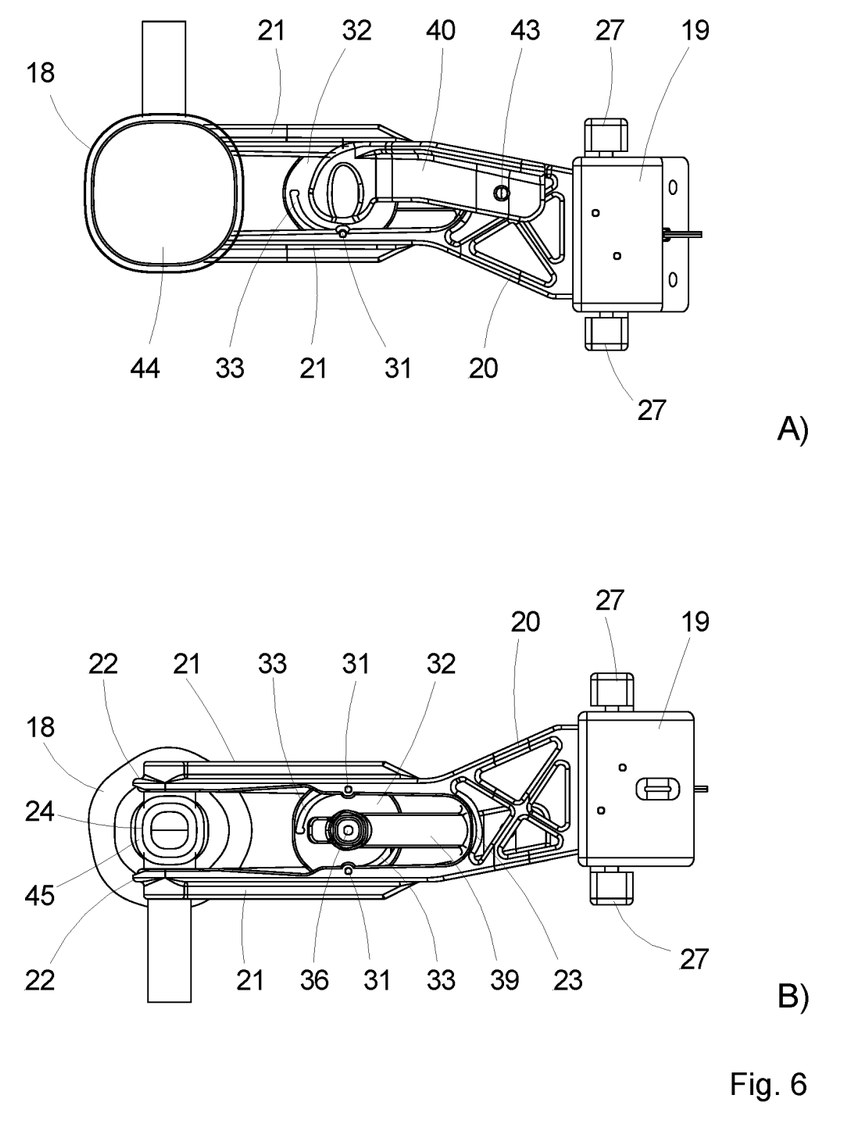

In order to make it easier to insert the receiving element 24 into the clamp element 20, the trocar holder therefore also has a clamp mechanism for opening and closing the limbs. The clamp mechanism comprises at least one pin 31, which is fixed in a limb 21 at an angle different from zero relative to the clamp plane. The drawings show, by way of example, two pins 31, which are fixed in the limbs 21 at angles different from zero relative to the clamp plane; a pin 31, which can be manufactured for example from stainless steel, is fixed in each limb 21. In FIG. 4 these pins 31 are shown outside the limbs 21 in the exploded drawing; in FIG. 5A), FIGS. 6A-B), FIG. 7 and FIG. 8 the pins 31 are inserted and fixed in the limbs 21. The fixing can be effected in a non-positive locking manner, a positive locking manner and/or in a material-locking manner. In the case shown here the pins 31 are connected to the limbs 21 in a non-positive locking and positive locking manner; opposite the openings in the limbs 21, into which they are driven, they have a light interference fit.

The clamp mechanism moreover comprises a guide element 32, in which a number of elongated holes 33, corresponding to the number of pins 31, with narrow sides 34 and long sides 35 are made. In the example shown the guide element 32 therefore has two elongated holes 33; the guide element 32 is represented in a view from below in FIG. 5C). The guide element 32 is movable in relation to a movement axis; the two pins 31 are guided in the elongated holes 33. An opening and closing of the limbs 21 is achieved by the two narrow sides 34 of each elongated hole 33 lying at different distances from the movement axis. The movement axis can be a displacement axis, which lies in the clamp plane and is spaced apart equally from both limbs 21, i.e., it intersects a point in the centre of the spine and a point at half the distance between the two tips 22, thus it lies parallel to the limbs 21. The guide element is then designed for example as a carriage, and a movement of the at least one pin 21 relative to the elongated hole 33 from the narrow side lying closer to the movement axis to the narrow side lying further from the movement axis opens the limbs 21 or the clamp; a reversed movement closes the clamp.

Another possibility, which makes an even more compact and stable configuration possible and which is realized in the examples represented in the drawings, is to design the movement axis as a second rotational axis 36; this second rotational axis lies perpendicular to the clamp plane, perpendicular to the page plane in FIGS. 5-8. The at least one elongated hole 33 is then at least partially curved. Here also, the two narrow sides 34 of each elongated hole 35 lie at different distances from the second rotational axis, a rotation of the guide element 32—shown by way of example in FIG. 5C)—brings about a relative movement between the pins 31 and the elongated holes 33 between the narrow sides 34 and, due to the different distances of the narrow sides 34 in relation to the second rotational axis 36, an opening of the clamp or a closing of the clamp is achieved by the corresponding movement of the limbs 21 during rotation of the guide element 32 about the rotational axis 36; the second rotational axis extends through the guide element 32.

In the undeflected state, i.e., in the closed state, the limbs 21 are in their rest position, i.e., no structure-related, internal restoring forces are acting on them. In order to make it easier to close the clamp, it is therefore advantageous if the area of the at least one elongated hole 33 which lies closer to the narrow side 34 that in turn lies closer to the second rotational axis 36 and defines the closed state of the clamp is designed as a straight section 37 of the elongated hole 33; this straight section 37 has no curvature and acts as a so-called dead area, as no adjustment takes place in this area. In this way possible manufacturing tolerances can be taken into account and it can be ensured that the guide element 32 can be brought into a rest position and fixed there. The pins 31 here are arranged perpendicular to the clamp plane, as is the second rotational axis 36. Opposite the elongated holes 33 the pins 31 can have a light interference fit, in order to prevent an involuntary adjustment. As an alternative or in addition, the guide element 32 can also be fixed in the two end positions which define the maximum possible opening and the closed clamp. In order to fix the clamp in the opened state and to make a safe replacement of the receiving element 24 possible, the elongated holes 33 lying closer to the movement axis have an indentation 38, in which the respective pin 31 can engage because of the intrinsic restoring force of the clamp, in the area of the narrow sides 34 that correspond to the opened clamp. Also in the area of the other narrow side 34, it is possible to provide such an indentation if the limbs 21 of the clamp element 20 are always to remain pretensioned, thus are prevented by the guide element 32 from reaching a rest position in which no restoring force is acting. In this case, the straight section 37 of the elongated hole 33 can also be dispensed with.

Figure 8:
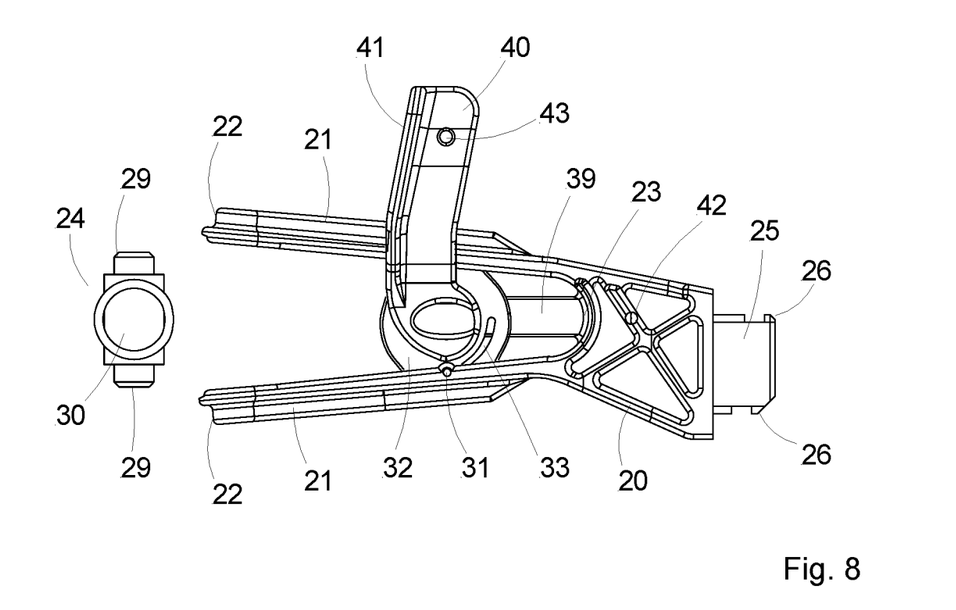

In the embodiment shown here, the guide element 32 is rotatably secured on a tongue 39 connected to the clamp element 20—represented by way of example in FIG. 5A), FIG. 6B) and FIG. 8. Through the use of the tongue 39 the stability of the trocar holder is substantially increased and the rotation of the guide element 32 is made easier, as the fixing on the tongue 39 also precludes a canting. The tongue 39 is preferably formed on the spine 23 of the clamp element 20 and preferably integrally with it, with the result that the guide element 32 remains stationary in relation to the spine 23 when the limbs 21 are being opened or closed.

In particular in the case of a guide element 32 as is shown here among other things in FIG. 5C) and which is rotated about a second rotational axis 36, it is advantageous if the guide element 32 has a lever 40 for actuating the clamp mechanism, as then the effort to be expended by the user is reduced and operation in general is made easier. In principle, it is also possible for example to increase the diameter of the guide element 32 designed disc-shaped here such that it extends beyond the distance between the two limbs 21 even more clearly than shown in FIG. 3, and a user can turn it from the outside by gripping the circumference of the guide element 32, which for this can be provided with grooves or other elements which help to better grip the guide element 32.

Figure 7:
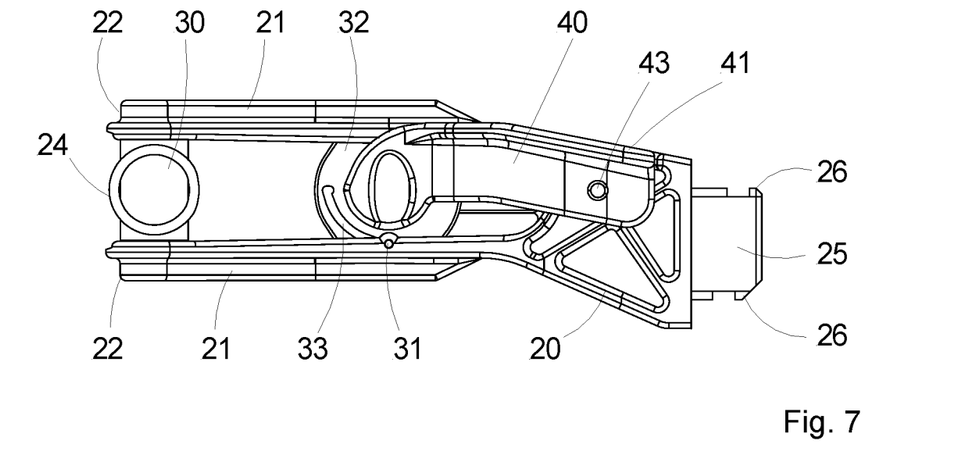

In the embodiment shown here, the guide element 32 has a lever 40. As regards FIG. 7 and FIG. 8, FIG. 7 shows the clamp element 20 from above with the lever in closed position and FIG. 8 shows the clamp element 20 with the lever 40 and the limbs 21 in opened position. FIG. 5C) shows the guide element 32 with the lever 40 attached thereto in a view from below. The lever 40 can also be seen in the exploded drawing in FIG. 4. On the lever 40, a grip element 41 is formed which can be seen in particular in the perspective drawings in FIG. 3 and FIG. 4. This makes it easier to operate the lever 40.

In order to fix the guide element 32 in the opened position, on their inner side, i.e., on the long side 35 that lies closer to the movement axis—here the second rotational axis 36—the elongated holes have indentations 38 in the area of the corresponding narrow sides 34 which correspond to the opened state, as already described above. Corresponding indentations 38, as an alternative or in addition to the closed state, can also be made at the other narrow side 34 and the other long side 35, wherein a hold therein is only secured when the clamp is under pretension.

In addition or as an alternative, fixing means, which are preferably formed as a snap-on connection, by means of which the lever 40 is secured in its position at least when the limbs 21 are closed, are advantageously formed or arranged on the lever 40 and on the clamp element 20. By way of example the snap-on connection here comprises a snap-in catch 42 arranged on the clamp element in the area of the spine 23 and a snap-in hole 43 corresponding to the snap-in catch 42 and formed on the lever 40. In this way, the lever 40 and thus also the guide element 32 are secured against involuntary opening when the clamp is closed, which is advantageous in particular when the clamp is not under pretension.

As an alternative to the embodiment shown in FIG. 7 and FIG. 8 of the clamp mechanism, it is also possible to use, instead of the pins 31, eccentric elements, which are arranged eccentrically with respect to the second rotational axis 36 on the guide element 22. These can be formed separately on the guide element 22 and for example have the shape of cylinders, which are arranged for example in the area of the narrow sides 34 that lie further away from the second rotational axis 36. However, they can also follow the shape of the elongated holes 33 and be formed as curved, oblong elevations. Finally, they can also be integrated in the area of the lever 40 which connects the lever 40 to the guide element 22, i.e., the area around the second rotational axis 36. The curves or rounded surfaces of this area which are perpendicular to the page plane here in FIG. 7 and FIG. 8 can then be formed with corresponding curvatures and larger. In all embodiments of the eccentric elements, the limbs 31 are opened or closed by the action of the eccentric element during a rotation of the guide element 22 about the second rotational axis 36.

This last-named embodiment can also be combined with the embodiment with pins in order to guarantee a better security. Otherwise, in the embodiment with eccentric elements, the pins 31 can also be dispensed with, which simplifies production and makes it more cost-effective, as metal parts are then no longer needed for the clamp mechanism.

Figure 9:
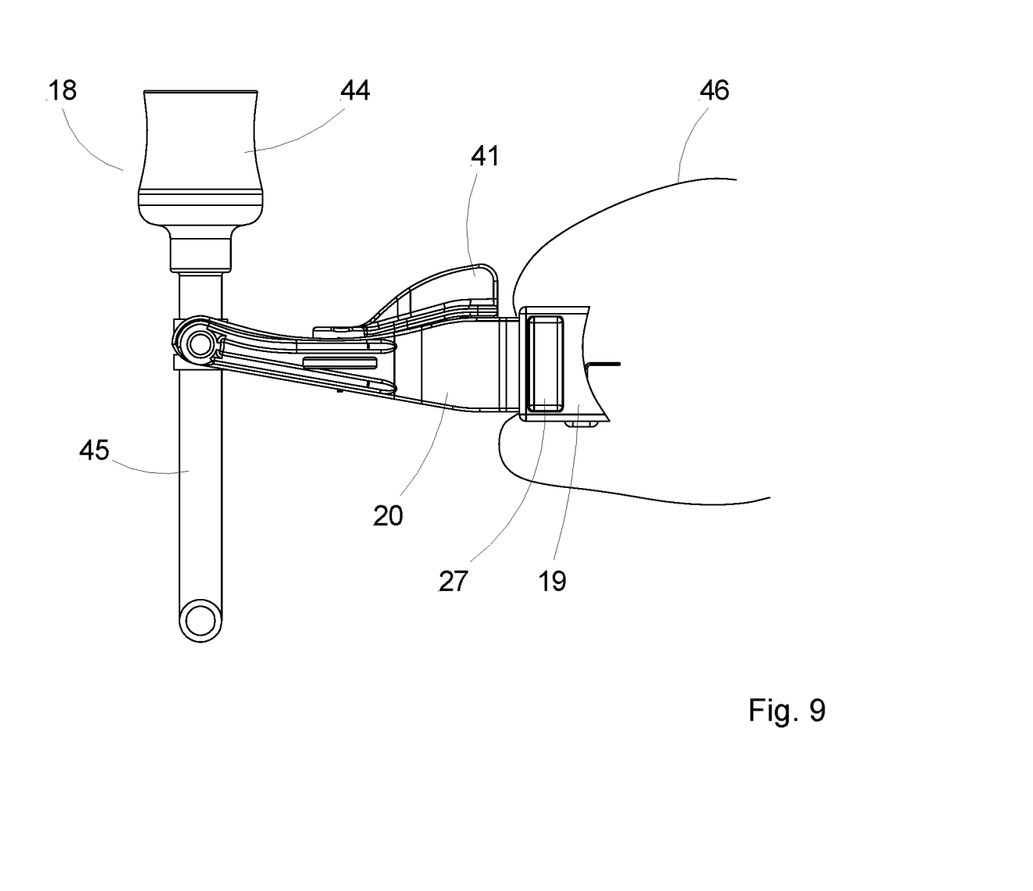

Finally, FIG. 9 shows the trocar holder with a sterilization film 46, which is arranged between the base element 19 and the clamp element 20. Before operation, before the clamp element 20 and the base element 19 are put together, this can be placed between them; the sterilization film 46 is then fixed in the assembled state by the snap-fit connection. However, the sterilization film 46 can also be non-detachably connected to the clamp element 20, if the latter—in combination with the receiving element 24 and the trocar 18 as well as the clamp mechanism—is designed as a disposable element and was packaged in a sterile manner during production.

The above-described trocar holder makes a simple change of the receiving element 24 and thus a simple change between trocars 18 of different diameter possible because of its easy-to-use clamp function. Due to the additional degree of tilting freedom for the trocar 18, the stress on the patient's outer tissue is reduced, with the result that the device guiding the trocar holder can be designed more compact. A sterility boundary is produced between the clamp element 20 and the base element 19 through the use of a sterilization film, with the result that here the sterility area has a very great extent in relation to the distance from the patient, which guarantees the greatest possible safety. In particular, the clamp element 20, but also the base element 19 as well as further important parts such as the receiving element 24, guide element 32, lever 40 etc., are manufactured from plastic, with the result that a cost-effective production is possible and the clamp element 20 can also be designed as a disposable element, which additionally increases safety.

LIST OF REFERENCE NUMBERS

1 Pedestal
2 Supporting column

3 Boom
4 Fork structure
5 Manipulator
6 Instrument holder
7 Operating table
8 Table pedestal
9 Patient
10 Control device
11 Handle
12 Viewing device
13 Instrument support device
14 Carriage
15 First arm element
16 Second arm element
17 Third arm element
18 Trocar
19 Base element
20 Clamp element
21 Limb
22 Tip
23 Spine
24 Receiving element
25 Snap-fit element
26 Snap-fit catch
27 Push button
28 Radial-axial bearing
29 Axle's end area
30 Opening
31 Pin
32 Guide element
33 Elongated hole
34 Narrow side
35 Long side
36 Rotational axis
37 Straight section
38 Indentation
39 Tongue
40 Lever
41 Grip element
42 Snap-in catch
43 Snap-in hole
44 Instrument receiver
45 Feed-through element
46 Sterilization film

The invention claimed is:

1. A trocar holder for a manipulator of a robotic surgical system, comprising:
a base element for securing the trocar holder to the manipulator;
a clamp element which is replaceably connected to the base element via a coupling mechanism and on which two limbs, connected via a spine, movable relative to each other in a clamp plane and with free tips are formed;
a clamp mechanism for opening and closing the limbs; and
a receiving element for a trocar; a radial-axial bearing is formed in an area of the tips of each of the two limbs; the receiving element is formed as an axle and has a continuous opening perpendicular through the axle to feed the trocar through; wherein the receiving element is prevented from moving axially by the radial-axial bearings when the limbs are closed.

2. The trocar holder according to claim 1, wherein when the limbs are closed, the receiving element is held by the limbs rotatably about a first rotational axis lying in a clamp plane.

3. The trocar holder according to claim 1, wherein the coupling mechanism is formed as a quick-release fastener operable by hand without further aids, in the form of a snap-fit connection.

4. The trocar holder according to claim 1, wherein the clamp mechanism comprises at least one pin fixed at an angle different from zero relative to the clamp plane in one of the limbs; and
a guide element, movable along or about a movement axis relative to the clamp element, in which at least one elongated hole with narrow sides and long sides is made;
wherein the at least one pin is guided in the at least one elongated hole;
wherein the two narrow sides of the at least one elongated hole lie at different distances from the movement axis, with the result that the at least one limb opens or closes during movement of the guide element along or about the movement axis.

5. The trocar holder according to claim 4, wherein the movement axis lies in the clamp plane and is spaced apart equally from both limbs, and the guide element is formed as a guide carriage, which is displaceable along the movement axis.

6. The trocar holder according to claim 4, wherein the movement axis is formed as a second rotational axis, which forms an angle different from zero with the clamp plane, and the guide element is rotatable about the second rotational axis, wherein the at least one elongated hole is at least partially curved.

7. The trocar holder according to claim 6, wherein the guide element is secured on a tongue connected to the clamp element.

8. The trocar holder according to claim 7, wherein the tongue is formed on the spine of the clamp element.

9. The trocar holder according to claim 6, wherein the second rotational axis and/or the at least one pin is arranged perpendicular to the clamp plane.

10. The trocar holder according to claim 4, wherein the clamp element in each of the two limbs comprises a pin fixed therein.

11. The trocar holder according to claim 4, wherein the pins have an interference fit relative to the elongated holes.

12. The trocar holder according to claim 4, wherein on the long side that faces the movement axis the at least one elongated hole has an indentation in the direction of the movement axis, in which the at least one pin engages when the limbs are opened, in the area of the narrow side lying further removed from the movement axis.

13. The trocar holder according to claim 4, wherein the guide element has a lever for actuating the clamp mechanism.

14. The trocar holder according to claim 13, wherein a connector by means of which the lever is secured in its position at least when the limbs are closed, is formed on the lever and on the clamp element.

15. The trocar holder of claim 14, wherein the connector comprises a snap-on connector.

16. The trocar holder according to claim 1, wherein the clamp mechanism comprises a guide element rotatable about a second rotational axis forming an angle different from zero with the clamp plane, wherein at least one eccentric element arranged eccentrically with respect to the second rotational axis is attached to the guide element, with the result that at least one of the limbs opens or closes due to the action of the eccentric element when the guide element is rotated about the second rotational axis.

17. The trocar holder according to claim 1, wherein:
at least the clamp element, the base element and the receiving element are manufactured from plastic; and/or
the limbs and the spine of the clamp element are formed integrally; and/or
at least one of the limbs is connected in a spring-loaded manner to the spine.

18. The trocar holder according to claim 1, wherein a sterilization film is fixed between the base element and the clamp element, wherein at least the clamp element, the receiving element and the clamp mechanism are designed sterile.

19. The trocar holder according to claim 1, wherein the receiving element is permanently connected to a trocar.

* * * * *